(12) United States Patent
Weihermüller

(10) Patent No.: US 6,666,837 B2
(45) Date of Patent: Dec. 23, 2003

(54) ORTHOSIS JOINT

(75) Inventor: Michael Weihermüller, Bayreuth (DE)

(73) Assignee: Medi Bayreuth Weihermuller & Voightman GmbH & Co. KG, Bayreuth (DE)

( * ) Notice: Subject to any disclaimer, the term of this patent is extended or adjusted under 35 U.S.C. 154(b) by 0 days.

(21) Appl. No.: 09/837,635

(22) Filed: Apr. 17, 2001

(65) Prior Publication Data
US 2002/0026136 A1 Feb. 28, 2002

Related U.S. Application Data

(63) Continuation of application No. PCT/DE00/02385, filed on Jul. 22, 2000.

(30) Foreign Application Priority Data

Aug. 17, 1999 (DE) .................. 299 14 375 U

(51) Int. Cl.$^7$ ................................ A61F 5/00
(52) U.S. Cl. ................ 602/16; 602/20; 602/26
(58) Field of Search ................. 602/16, 26, 5, 602/20, 23; 128/878, 882

(56) References Cited

U.S. PATENT DOCUMENTS

| 5,031,606 A | 7/1991 | Ring, Sr. | |
|---|---|---|---|
| 5,036,837 A | 8/1991 | Mitchell et al. | |
| 5,437,611 A | * 8/1995 | Stern | 602/16 |
| 5,437,619 A | * 8/1995 | Malewicz et al. | 602/20 |
| 5,749,840 A | * 5/1998 | Mitchell et al. | 602/5 |
| 5,899,869 A | * 5/1999 | Barrack et al. | 602/16 |
| 6,129,690 A | * 10/2000 | Hamlin et al. | 602/16 |
| 6,309,368 B1 | * 10/2001 | Herzberg et al. | 602/26 |

FOREIGN PATENT DOCUMENTS

| EP | 0693276 A1 | 1/1996 |
|---|---|---|
| EP | 0841044 A1 | 5/1998 |

* cited by examiner

Primary Examiner—Nicholas D. Lucchesi
Assistant Examiner—Quang D. Thanh
(74) Attorney, Agent, or Firm—Thomas R. Vigil; Welsh & Katz, Ltd.

(57) ABSTRACT

The orthosis joint is for orthoses for two parts of the body which can be bent and stretched against each other, such as knee or arm orthoses. The orthosis joint rotationally connects two splints that are each connected to upper and lower parts of the orthosis that can be fastened to the respective part of the body and comprises a pair of splints with orthosis joints that are arranged laterally and/or centrally, respectively, on the orthosis, and the splints mesh with each other at their ends by way of one or several common pins or by teeth are provided at the ends in the orthosis joint and adjustable end stops are provided for extension and/or flexion. The end stops are adjustable over one or several angular ranges $\delta$ and that flexion or extension, respectively, in the orthosis joint undergoes constant or dynamic braking within an angular range of $\delta+\alpha$ or $\delta-\alpha$, $\alpha$ representing an angle from 3 to 25°.

9 Claims, 4 Drawing Sheets

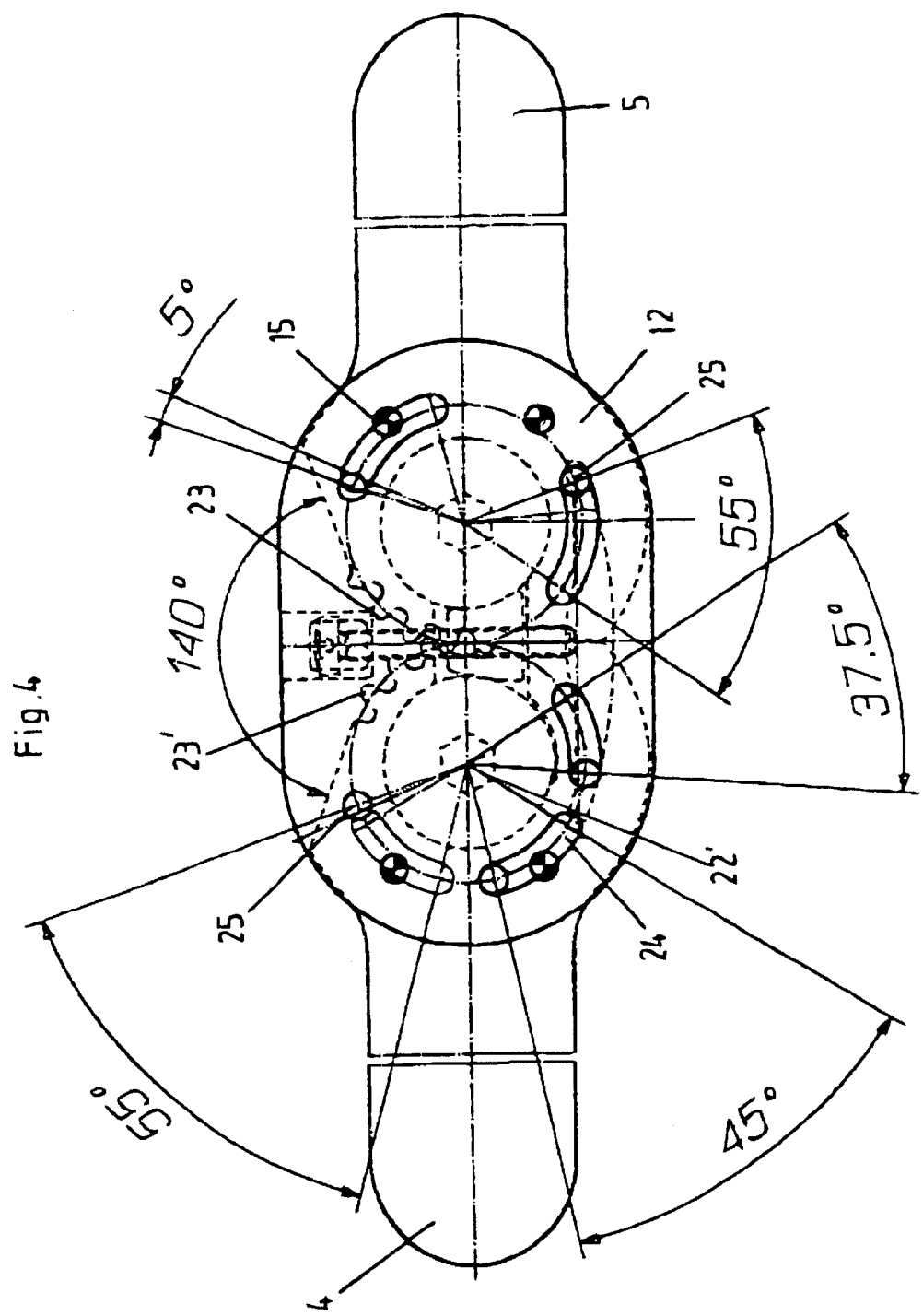

ORTHOSIS JOINT

CROSS-REFERENCE TO RELATED APPLICATIONS

This application is a Continuation of PCT Application No. PCT/DE 00/02385 filed Jul. 22, 2000 which claims priority from German Patent Application No. 299 14 375.9 filed Aug. 17, 1999.

BACKGROUND OF THE INVENTION

1. Field of the Invention

The present invention relates to an orthosis joint for orthoses for two parts of the body which can be bent and stretched against each other, such as knee or arm orthoses, is provided, wherein the orthosis joint rotationally connects two splints that are each connected to upper and lower parts of the orthosis that can be fastened to the respective part of the body, wherein a pair of splints with orthosis joints are arranged laterally and/or centrally, respectively, on the orthosis, wherein the splints mesh with each other at their ends by way of one or severa common pins or by teeth provided at the ends in the orthosis joint, wherein adjustable end stops for extension, $\delta=0°$, and/or flexion, $\delta=90°$, are provided, and wherein the end stops are adjustable over one or several angular ranges $\delta$ so that flexion or extension respectively in the orthosis joint undergoes constant or dynamic braking with an angular range or $\delta$ so that flexion or extension respectively in the orthosis joint undergoes constant or dynamic braking within an angular range of $\delta+\alpha$ or $\delta-\alpha$, $\alpha$ representing an angle from 3 to 25°. As a result, a non-braking range of 84° maximum (($\delta$ flexion=90°)−($\alpha$=3°))−(($\delta$ extension=0°)+($\alpha$=3°)) and 40° minimum (($\delta$ flexion=90°)−($\alpha$=25°))−(($\delta$ extension=0°)+($\alpha$=25°)) is established.

2. Description of the Prior Art

EPA 0841 044, for example, discloses an adjustable orthosis joint. Here, the force of a spring is applied to a certain pivoting range of the orthosis that can be adjusted in advance, wherein the action of the spring can be canceled for allowing extension and flexion movements to occur without the application of any force.

EPA 693 276 discloses an orthosis joint for orthoses for two parts of the body which can be bent and stretched against each other, such as knee or arm orthoses, wherein the orthosis joint rotationally connects two splints that are each connect to upper and lower parts of the orthosis that can be fastened to the respective part of the body and wherein a pair of splints with orthosis joints are arranged laterally and/or centrally respectively on the orthosis, wherein the splints mesh with each other at their ends by way of one or several common pins or by teeth provided at the ends in the orthosis joint and wherein adjustable end stops for extension and/or flexion are provided. EPA 633 007 shows a similar structure, but with latches.

BRIEF SUMMARY OF THE INVENTION

It is the object of the present invention to provide an orthosis joint, the extension and flexion range of which being adjustable, wherein motion occurs within a certain range without the application of any force until it meets with a counteracting, braking force prior to reaching the respective end point. This is to serve the purpose of avoiding sudden stress on the ligaments, more specifically on the cruciate ligaments, by causing the patient to meet with perceptible resistance before he reaches the end point. Simultaneously, the return to a neutral position is encouraged as a result thereof.

The solution of this object is achieved by an orthosis joint for orthoses for two parts of the body which can be bent and stretched against each other, such as knee or arm orthoses According to the invention, an orthosis joint is provided for orthoses for two parts of the body which can be bent and stretched against each other, such as knee or arm orthoses, is provided, wherein the orthosis joint rotationally connects two splints that are each connected to upper and lower parts of the orthosis that can be fastened to the respective part of the body and wherein a pair of splints with orthosis joints are arranged laterally and/or centrally, respectively, on the orthosis, wherein the splints mesh with each other at their ends by way of one or several common pins or by teeth provided at the ends in the orthosis joint and wherein adjustable end stops for extension and/or flexion are provided, wherein the end stops are adjustable over one or several angular ranges $\delta$ so that flexion or extension respectively in the orthosis joint undergoes constant or dynamic braking within an angular range of $\delta+\alpha$ or $\delta-\alpha$, $\alpha$ representing an angle from 3 to 25°

Braking may occur pneumatically, hydraulically or by way of an elastic element, for example, a catch releasing a pneumatic or hydraulic member accommodated on the orthosis or joining the elastic element for cooperation upon reaching the certain angular range. The hydraulic member can operate on a basis of low or high viscosity. Braking may also occur mechanically by the friction of at least two parts that mesh with one another upon reaching the certain angular range, wherein plates coated with friction linings may be used, the bearing pressure of which can be made adjustable. Cooperation of friction and elastic elements is also possible like, e.g. a key to which the force of a spring is applied, wherein said force of the spring can be adjustable. The elastic element can be a spring with a constant or dynamic characteristic curve or consist of a natural or synthetic elastomer. The initial position that is, substantially the straightening of the joint, is recovered without a braking force being applied, said braking force only acting in the direction of extension or flexion.

According to a preferred embodiment of the invention, the orthosis joint comprises, in a conventional way, the end pieces of two splints that are attached to the respective orthosis parts and are provided at their ends with meshing teeth, the end pieces of the splints pivoting on respective pins of a base plate connecting said pins. According to the invention, at least one pin is non-rotatably linked to at least one catch which, upon reaching the certain angular range, acts either directly or by way of an intermediate member upon one or several elastic elements. The catch may, for example, be a hook that is connected to the end of a spiral spring which is carried in a casing on the base plate. According to one preferred embodiment of the invention, the end pieces are non-rotatably linked to the pins, the catch being an eccentric disk which is non-rotatably linked to the pins and which is brought to frictionally engage an intermediate member after a preset path, the disk eventually causing, in rotational direction of the disk, movement of the intermediate member in the direction of the force of a spring acting upon said intermediate member. The intermediate member acts upon a compression spring, a leaf spring or an elastomer element, the force of the intermediate member that acts upon the spring or the elastomer element being adjustable. Adjustment is performed by way of a regulating screw by means of which a desired bias is realized between the intermediate member and the elastic element. The end stops are adjusted by way of bores or long holes in the end pieces, wherein pins that are stationarily arranged on a cover plate for the end pieces engage into said bores or holes.

BRIEF DESCRIPTION OF THE SEVERAL VIEWS OF THE DRAWING

The invention will be described more explicitly hereinafter with the help of exemplary embodiments illustrated in the Figures.

FIG. 4 shows a top view of the orthosis joint in which the upper cover plate has been omitted.

DETAILED DESCRIPTION OF THE INVENTION

Figure 1:
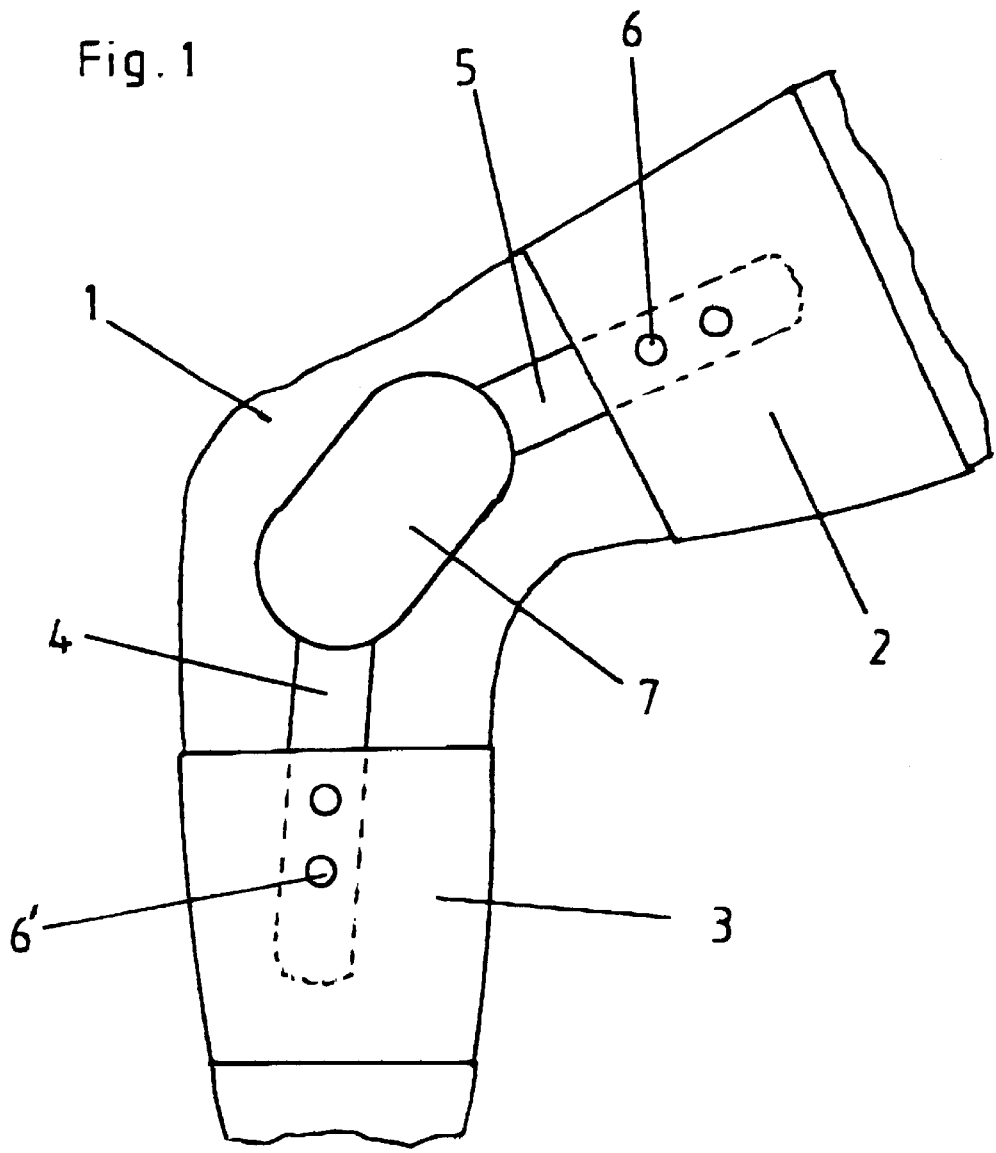
FIG. 1 shows schematically the accommodation of an orthosis in the region of the knee.

FIG. 1 shows a knee 1 wearing a knee orthosis. The knee orthosis consists of a holding part 2 for holding the thigh and a holding part 3 for holding the lower leg. Metal splints 4, 5 are respectively attached to the sides and to the center of the holding parts by means of rivets 6, the splint 5 of the holding part 2 for the thigh extending downward and the splint 4 of the holding part 3 for the lower leg extending upward. Both splints join in the orthosis joint 7 in which they are carried so as to be rotatable over a certain angular range and are engaged with each other via teeth.

Figure 2:
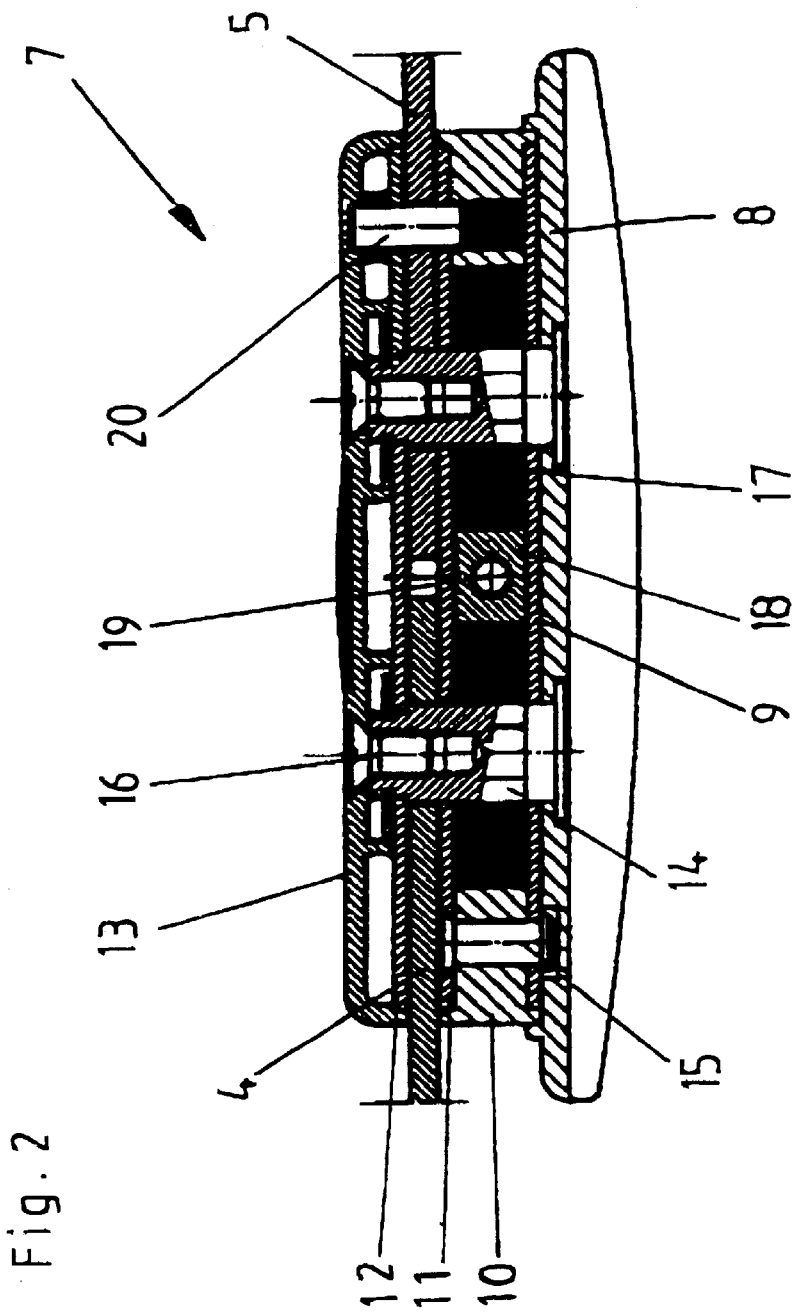
FIG. 2 shows a longitudinal section through the orthosis joint.

FIG. 2 shows the structure of the orthosis joint 7 in longitudinal section. It consists of a base plate 8 in which two hexagon pins 14 oriented upward are rotatably accommodated. A first intermediate plate 9 lies on the base plate, a flat casing 10 being adjacent said intermediate plate. The casing 10 houses the catching and braking mechanism that will be described more fully hereinafter. The casing is covered by a second intermediate plate 11 through which the hexagon pins 14 are rotatably threaded. The end pieces of the splints 4, 5 which are meshing by way of teeth are placed on the second intermediate plate 11 and below a third intermediate plate 12. The end pieces of the splints 4, 5 are rotatably connected to the hexagon pins 14 that are provided above the splints with shoulders by means of which they abut underneath the third intermediate plate 12, being rotatably threaded through said third plate by a tapered cylindrical end, though. A cover plate 13 is accommodated on a third intermediate plate 12, said cover plate being connected to the hexagon pins 14 by screws 16, said screws 16 being capable of rotating in the cover plate 13. The base plate 8 is connected to the two lower intermediate plates 9, 11 and to the casing 10 lying therein between by way of screws or pins 15 so that the orthosis joint 7 constitutes a unit which is secured from the top and from the bottom.

Figure 3:
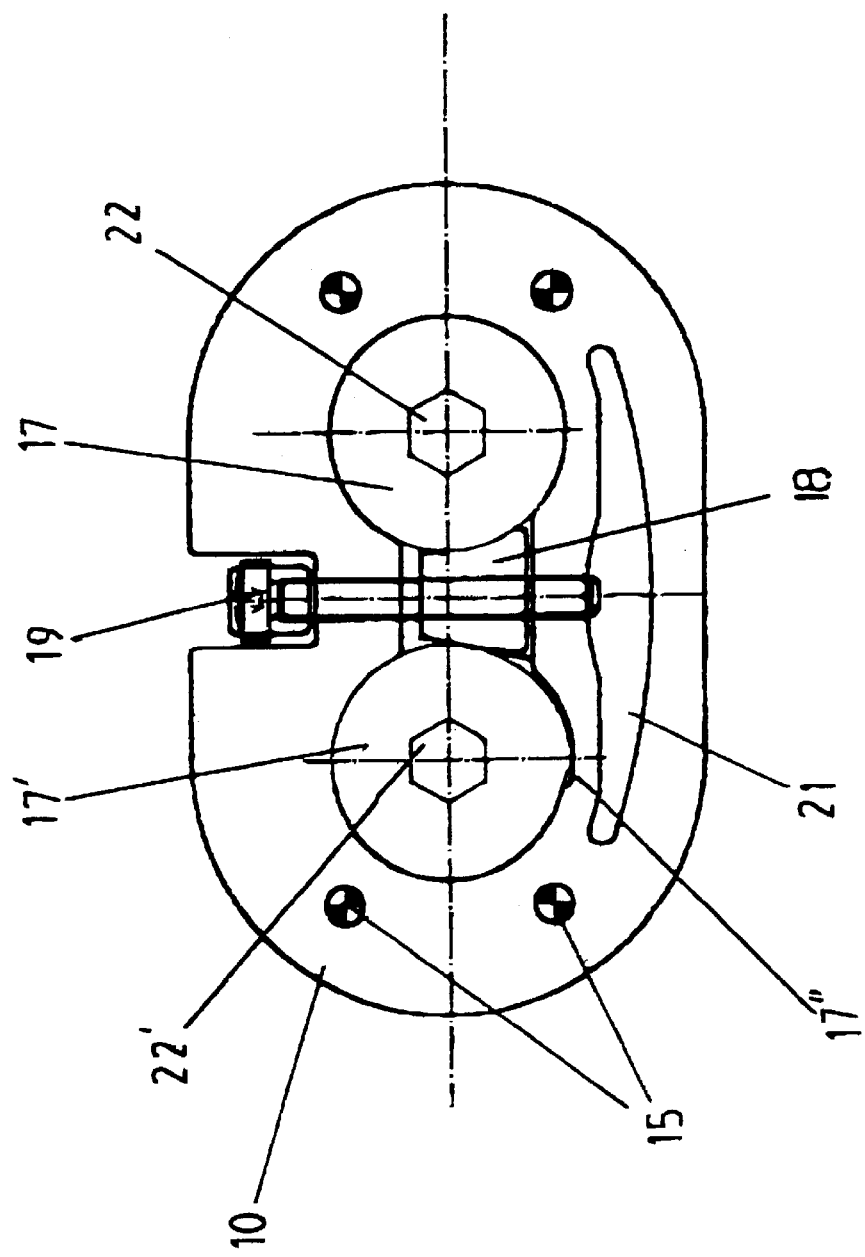
FIG. 3 shows a top view of the catching and braking mechanism of the orthosis joint.

FIG. 3 shows a top view of the casing 10 with its mechanics parts wherein all of the other elements of the orthosis joint have been omitted. It can be seen that four lower fastening pins 15 are arranged to the sides of the ends. Two recesses are provided in which two spaced apart disks 17, 17' are arranged in the longitudinal axis of the joint. The disks are provided with centrical hexagon bores 22, 22' by means of which they are non-rotatably plugged onto the hexagon pins (not shown here). The end pieces of the splints, which are not illustrated in the drawing herein, are also provided with such hexagon bores so that, when the splints are rotating toward each other, the disks 17, 17' are obliged to rotate as well. The right disk 17 is circular in shape whereas the left disk has an eccentric section 17'''. A key or intermediate shoe member 18 is arranged between the disks and runs with a threaded hole on a threaded bolt between the not shown intermediate plates in such a manner that it is secured from twisting. The threaded bolt or screw 19 is accommodated by its inner end on an elastic element 21 that applies the force of a spring onto said bolt and tries to urge it outward. In the process, the threaded bolt 19 takes the key 18 along, which, as a brake key, abuts with its faces on the outer contour of the disks 17, 17'. The deeper the threaded bolt 19 is screwed down, the higher the force exerted onto said bolt and the key 18. Were a substantially constant friction provided between the circular disk 17 and the key 18, the eccentrically increasing outer periphery of the left disk 17' would experience an ever increasing friction with the key 18 when the left disk 17 rotates counterclockwise, said friction being simultaneously transmitted to the circular disk 17 so that an increasing braking force would develop between the key and the disks until locking occurs if the path of the disks were not limited by the measures described herein after. Thanks to this limitation, a region of reduced friction is followed by a region of higher friction upon engagement of one portion of the eccentric region of the left disk, which means for the user that he first feels no or but little resistance on starting flexion or extension, this condition being replaced by perceptible braking taking place before the end position is achieved. The shape of the key 18 causes it to brake in but one direction in which it is pressed against the disks. In the other direction, i.e., on the return, the key exerts no braking force.

FIG. 4 shows the end pieces of the splints 4, 5 with their meshing teeth 23, 23'. Both end pieces are provided with hexagon bores 22' by means of which they are non-rotatably connected to the (not shown) hexagon pins in the way described hereinabove. As a result thereof, they are connected to the catching and braking mechanism that was described with reference to FIG. 3. The third intermediate plate 12, which is provided with a number of bores 25, as well as the ends of the lower fastening pins 15 are placed on the end pieces. The long holes 24 represented here are oriented concentrically to the rotational axes of the splints ends and are not accommodated in the intermediate plate 12 but in the end pieces of the splints, which has been wrongly represented in the drawing for purposes of clarity in order to better illustrate their cooperation with the bores 25. The rotational axes of the splints 4, 5 substantially lie in the longitudinal axis of the hexagon bores 22'. To adjust the end stops for the splints 4, 5, pins (pins 20 in FIG. 2) can be threaded through the bores 25 provided in the upper cover. These pins then run in desired long holes so that admissible flexion and extension angles may be chosen for the knee. Certain exemplary angular ranges are represented here. Since the arrangement of bores and long holes is discretional, other angular ranges are possible of course. For the user, the above mentioned object is achieved by the cooperation of the catching and braking mechanism with the end stops.

I claim:

1. An orthosis joint (7) for orthoses for two parts of a body which can be bent and stretched against each other, namely one of a knee or an arm orthoses, wherein the orthosis joint (7) rotationally connects two splints (4, 5) that are each connected, respectively, to upper and lower holding parts (2 and 3) adapted to be fastened, respectively, to a respective part of the body by extending the holding part (2, 3) around that part of the body and wherein each splint (4, 5) is fixed at one end to the holding part (2 or 3) and meshes at a second end in the orthosis joint (7) with the second end of the other splint (5, 4) by means of one of pins or teeth (23, 23') provided at each second end of each splint (4, 5) in the orthosis joint (7) and wherein end stops (20) for limiting extension and flexion are provided, fixed in a cover plate 13, characterized in that a braking mechanism is provided in a housing (10) in the orthosis joint (7) and includes an intermediate shoe member (18) supported on a base plate (8) in the housing (10) and at least one of a circular disk (17) for constant braking or an eccentric disk (17') for gradual or dynamic braking which is positioned adjacent said intermediate shoe member (18) in said housing (10'), said at least one disk (17 or 17') being mounted to rotate about an axis of rotation of one of said second ends of said splints (4, 5) and against said intermediate shoe member (18) to provide a constant or gradual braking force and in that said end stops (20) are received in one of several arcuate slots 24 in one of said second ends of said splints (4, 5), said arcuate slots 24 allowing movement of the splints (4, 5) until an end stop (20) engages an end of an arcuate slot (24) and over a limited range of motion established by the end stops (20) and defined by an angular range $\delta$ which is between $\delta 1$, extension, of 0° and $\delta 2$, flexion, of 90° and that extension and flexion, respectively, in the orthosis joint (7) undergoes one of constant or dynamic braking within a certain angular range of ($\delta$, flexion−$\alpha$) or ($\delta$, extension+$\alpha$), where $\alpha$ represents an angle between 3° and 25° so that a non-braking range of 84° maximum (($\delta$flexion=90°)−($\alpha$=3°))−(($\delta$ extension=0°)+($\alpha$=3°)) can be established and a non-braking range at 40° minimum (($\delta$ flexion=90°)−($\alpha$=25°))−(($\delta$ extension=0°)+($\alpha$=25°)) can be established.

2. An orthosis joint according to claim 1, characterized in that an elastic element (21) forming a spring is placed in the orthosis joint (7) and has one of a constant or dynamic characteristic curve.

3. An orthosis joint according to claim 2, characterized in that the elastic element (21) comprise, an elastomeric element.

4. An orthosis joint according to claim 1, characterized in that the orthosis joint (7) comprises the second ends of the splints (4, 5) which pivot on respective pins (14) mounted in the base plate (8) of said orthosis joint (7).

5. An orthosis joint according to claim 4, characterized in that at least one pin (14) on the axis of rotation of said second end of one of said splints (4 or 5) is non-rotatably linked to at learnt one of said disks (17, 17').

6. An orthosis joint according to claim 5, characterized by including intermediate plates (9, 11 and 12) which are non-rotatably linked to the pins (14), the at least one disk being an eccentric disk (17') which is non-rotatably linked to the pins (14), wherein the braking force occurs when the disk (17') is brought to frictionally engage the intermediate shoe member (18) after movement of the splints (4, 5) through a preset path, and the disk (17') then causing, in rotational direction of the disk, transverse movement of the intermediate shoe member (18) toward the disk (17 or 17") under a biasing force of an elastic element (21) acting upon said intermediate shoe member (18).

7. An orthosis joint according to claim 6, characterized in that the amount of braking force applied, can be adjusted according to the position of the intermediate shoe member (18) relative to the elastic element (21) by threading a screw (19) in the orthosis joint (7) through the intermediate shoe member (18) and against the elastic element (21).

8. An orthosis joint (7) for orthoses for two parts of a body which can be bent and stretched against each other, namely one of a knee or an arm orthoses, wherein the orthosis joint (7) rotationally connects two splints (4, 5) that are each connected, respectively, to upper and lower holding parts (2 and 3) adapted to be fastened, respectively, to a respective part of the body by extending the holding part (2, 3) around that part of the body and wherein each splint (4, 5) is fixed at one end to the holding part (2 or 3) and meshes at a second end in the orthosis joint (7) by means of one of pins or teeth (23, 23') provided at each second end of each splint (4, 5) in the orthosis joint (7) and wherein end stops (20) for limiting extension and flexion are provided, characterized in that a braking mechanism is provided in the orthosis joint (7) and includes braking means for exerting a braking force on the movement of the parts of the body as the splints (4, 5) move from an extension position where the splints (4 and 5) are in line with each other to a position of flexion where the splints (4, 5) are at an angle to each other and said braking means including a shoe member (18) and at least one of a circular disk (17) or an eccentric disk (17') positioned adjacent said shoe member (18) and associated with said second ends of said splints (4, 5) for placing an increasing braking force on the movement of the splints (4, 5) by the movement of the shoe member (18) against at least one of the disks (17 or 17') as the splints (4, 5) are moved relative to each other to provide a gradual increased braking force as the flexion angle increases and the extent of movement being defined by the end stops (20).

9. An orthosis joint (7) for orthoses for two parts of a body which can be bent and stretched against each other, namely one of a knee or an arm orthoses, wherein the orthosis joint (7) rotationally connects two splints (4, 5) that are each connected, respectively, to upper and lower holding parts (2 and 3) adapted to be fastened, respectively, to a respective part of the body by extending the holding part (2, 3) around that part of the body and wherein each splint (4, 5) is fixed at one end to the holding part (2 or 3) and meshes at a second end in the orthosis joint (7) by means of one of pins or teeth (23, 23') provided at each second end of each splint (4, 5) in the orthosis joint (7) and wherein end stops (20) for limiting extension and flexion are provided, characterized in that a braking mechanism is provided in the orthosis joint (7) and includes braking means for exerting a braking force on the movement of the parts of the body as the splints (4, 5) move from an extension position where the splints (4 and 5) are at an angle to each other to an extension position where the splints (4 and 5) are in line with each other and said braking means including a shoe member (18) and at least one of a circular disk (17) or an eccentric disk (17') positioned adjacent said shoe member (18) and associated with said second ends of said splints (4, 5) for placing an increasing braking force on the movement of the splints (4, 5) by the movement of the shoe member (18) against at least one of the disks (17 or 17') as the splints (4, 5) are moved relative to each other to provide a gradual increased braking force as the flexion angle decreases to zero and the extent of movement being defined by the end stops (20).

* * * * *